United States Patent [19]

Regnier et al.

[11] 4,243,753
[45] Jan. 6, 1981

[54] APPARATUS FOR ENZYME DETECTION

[75] Inventors: Frederick E. Regnier, West Lafayette, Ind.; Shung-Ho Chang, St. Louis, Mo.

[73] Assignee: Purdue Research Foundation, West Lafayette, Ind.

[21] Appl. No.: 881,577

[22] Filed: Feb. 27, 1978

Related U.S. Application Data

[63] Continuation of Ser. No. 674,510, Apr. 7, 1976, abandoned.

[51] Int. Cl.$^2$ .......................... C12M 1/40; C12M 1/34
[52] U.S. Cl. ......................................... 435/288; 435/4; 435/17; 435/21; 435/26; 435/291; 435/803; 435/808; 435/815; 210/198.2; 210/656; 422/59
[58] Field of Search ................ 195/103.5 R, 127, 115, 195/116, 63, 68; 210/198 C, 31 C; 261/94, 95, DIG. 72; 422/59; 435/4, 17, 21, 26, 288, 291, 803, 808, 814, 815

[56] References Cited

U.S. PATENT DOCUMENTS

| | | | |
|---|---|---|---|
| 3,170,969 | 2/1965 | Lerner et al. | 261/94 |
| 3,468,637 | 9/1969 | Hammond | 261/94 X |
| 3,493,218 | 2/1970 | Castellucci | 261/95 |
| 3,722,181 | 3/1973 | Kirkland et al. | 55/67 |
| 3,796,657 | 3/1974 | Pretorius et al. | 261/DIG. 72 X |
| 3,808,125 | 4/1974 | Good | 55/67 X |
| 3,838,011 | 9/1974 | Hagen et al. | 195/103.5 R |
| 3,956,065 | 5/1976 | Idaszak et al. | 195/116 X |
| 3,983,299 | 9/1976 | Regnier | 210/31 C X |

Primary Examiner—Robert J. Warden
Attorney, Agent, or Firm—John R. Nesbitt; Robert E. Harris

[57] ABSTRACT

An apparatus is disclosed for enzyme detection that is particularly well suited for high performance liquid chromatography. The apparatus is basically a flow-through enzyme detector that is capable of maintaining zero-order reaction kinetics with respect to substrate during enzyme detection and this results in a linear accumulation of product that can be readily measured to provide a dependable readout of detected enzymes. A sample in liquid form that may include one or more enzymes is coupled through a separation column to separate the enzymes, after which a reaction causing substrate is added and the resulting mixture is caused to flow through a reaction chamber, reaction products then being detected with the readout therefrom indicating the detected enzymes. The dimensions of the reaction chamber are dependent upon flow rates and must be selected to allow the mixture to remain in the chamber for a preselected reaction time. In addition, the chamber and packing material therein are selected to assure minimization of chromatographic profile distortion by band spreading as well as preventing separation of the components of the mixture passing therethrough. To this end, the chamber and packing material within the chamber must be of non-porous material, inert to proteins to be detected, and must assure even flow conditions.

13 Claims, 14 Drawing Figures

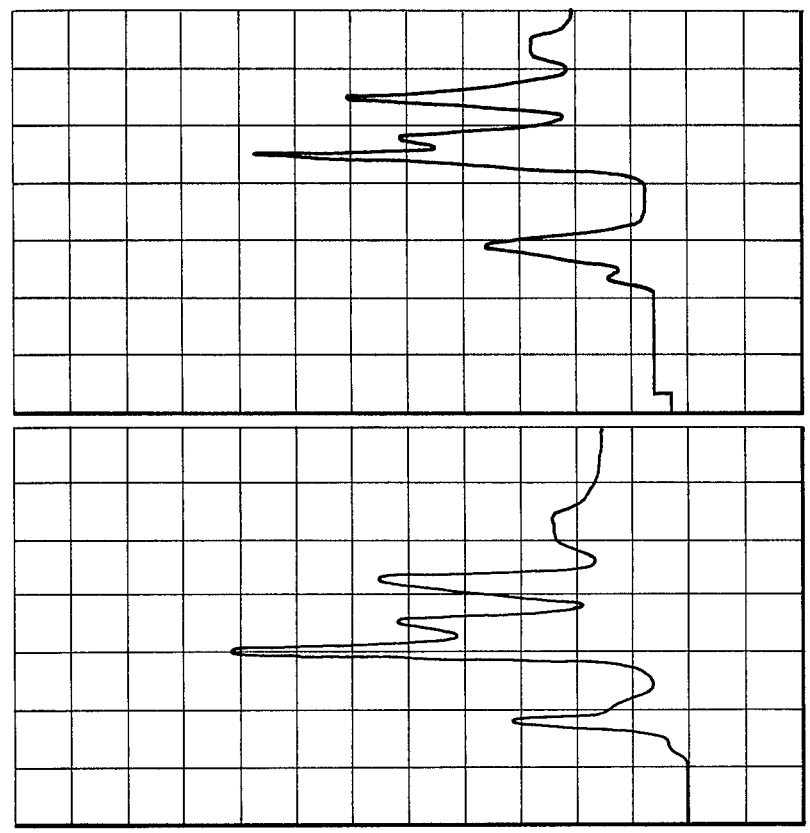
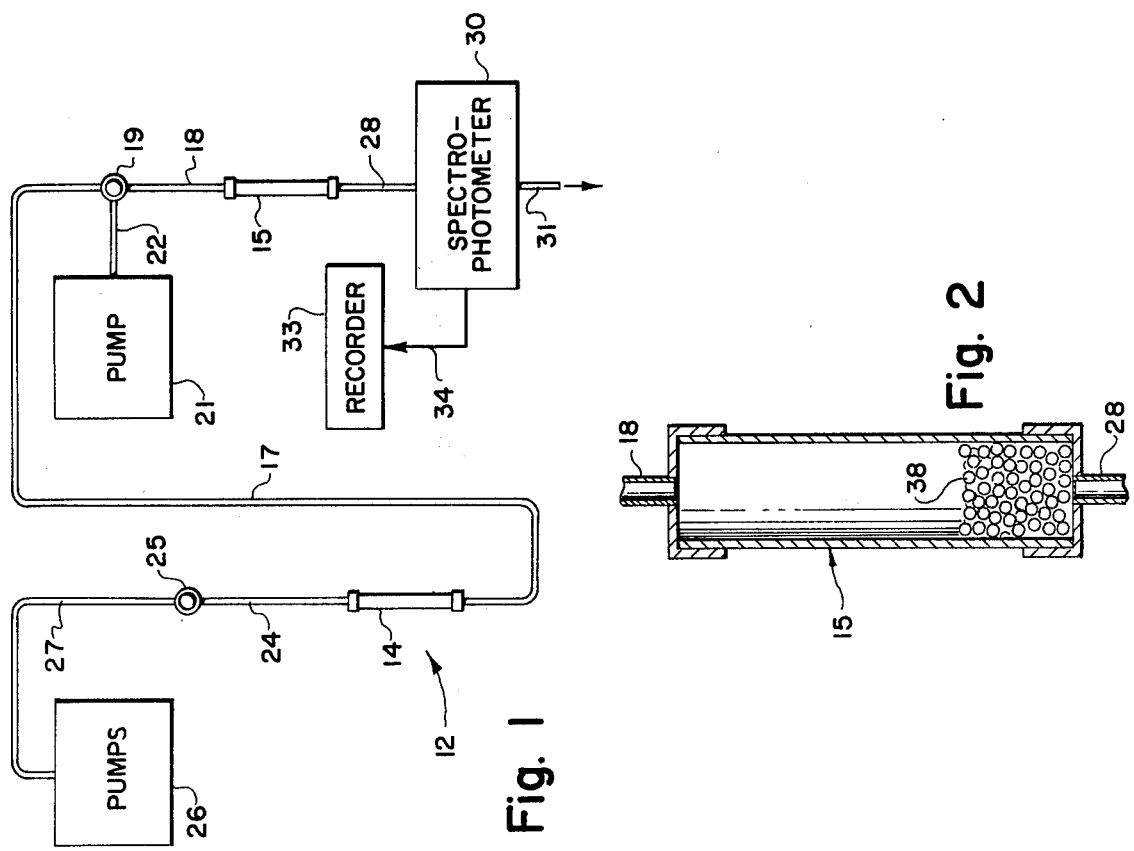

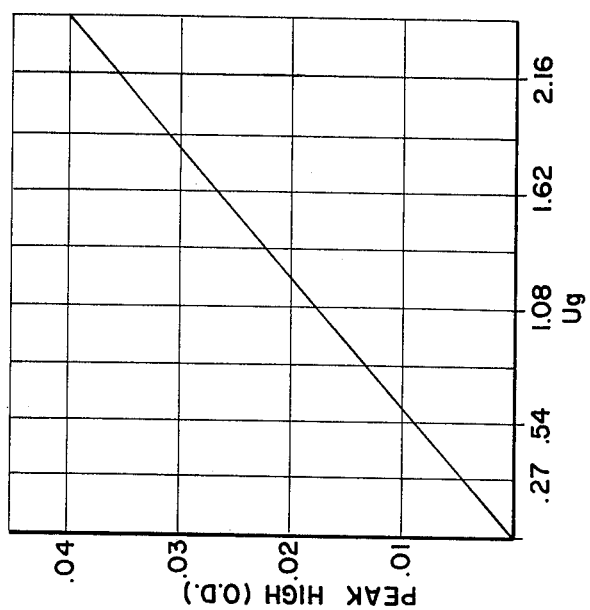
Fig. 6
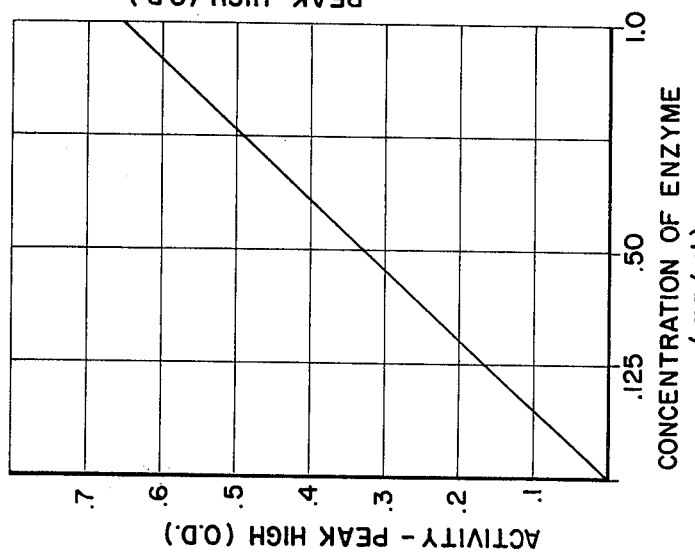
Fig. 5
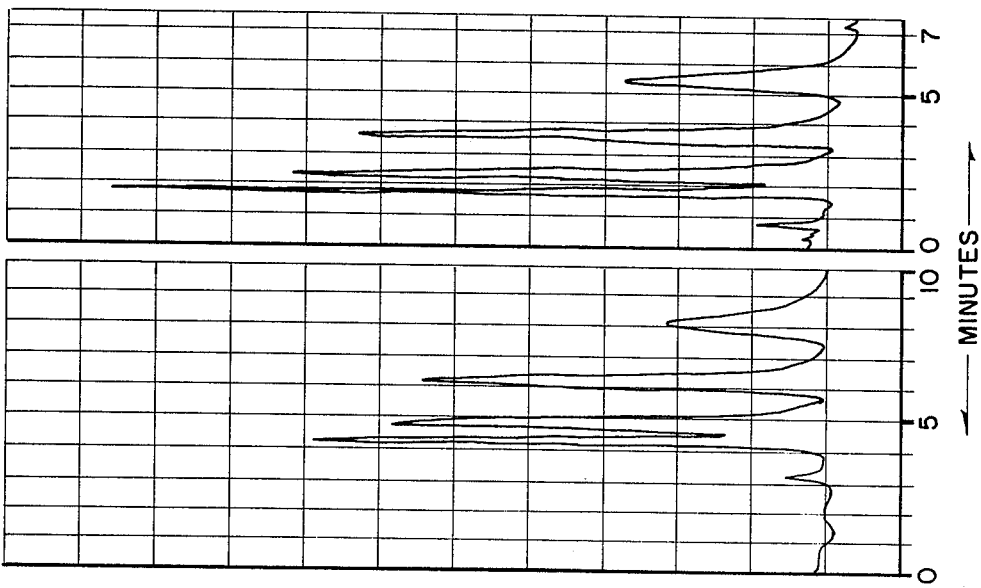
Fig. 4A
Fig. 4B

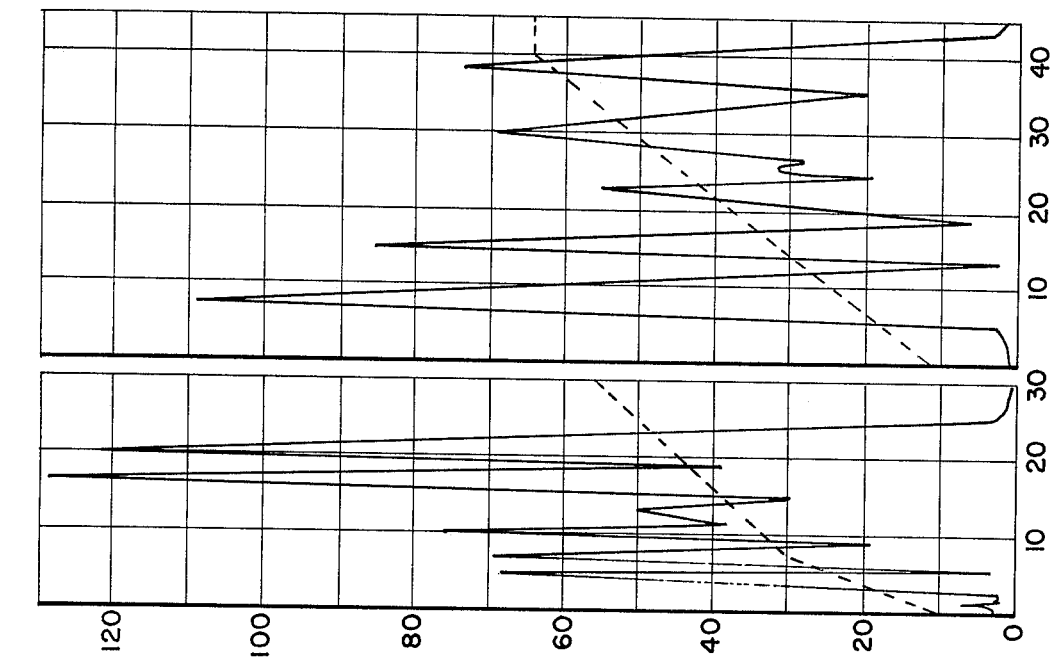
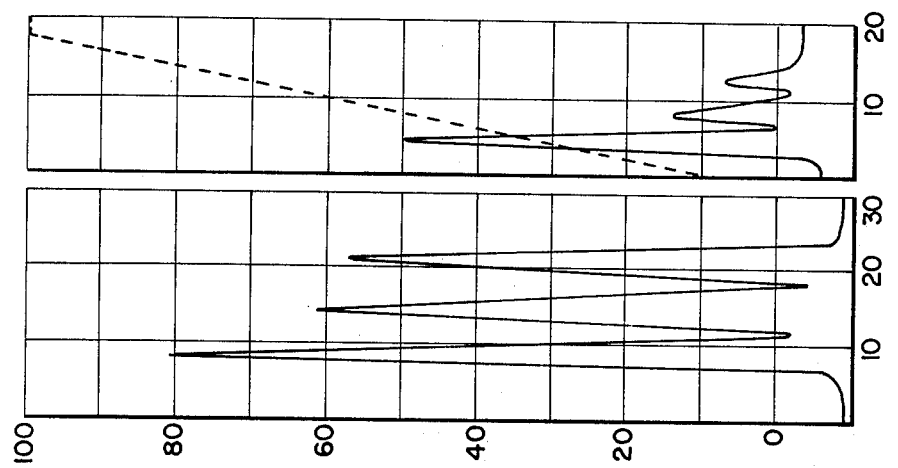
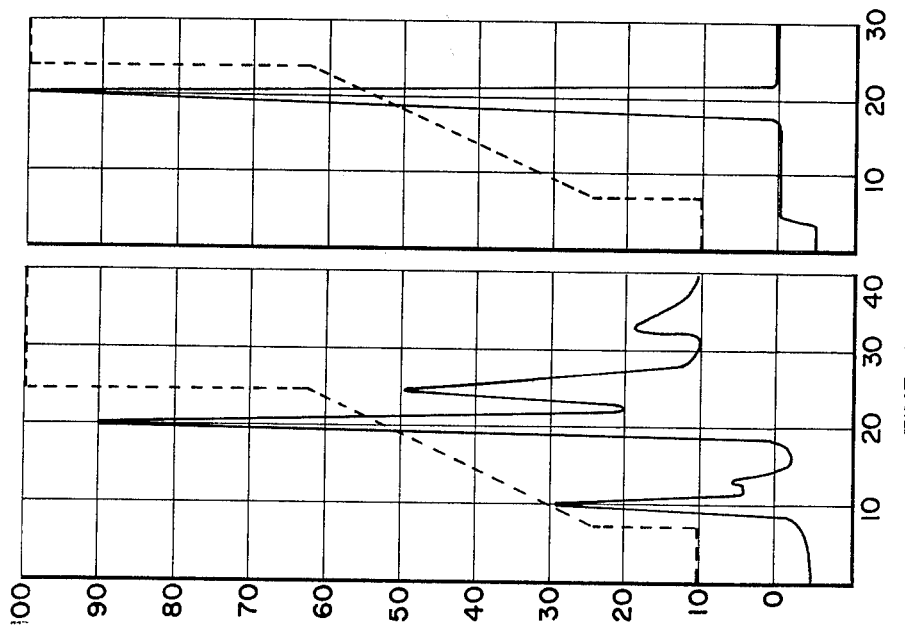
Fig. 7A  Fig. 7B  Fig. 8A  Fig. 8B  Fig. 9A  Fig. 9B

APPARATUS FOR ENZYME DETECTION

RELATED APPLICATION

This application is a continuation of our copending U.S. patent application, Ser. No. 674,510, filed Apr. 7, 1976, entitled "Apparatus for Enzyme Detector" and now abandoned.

FIELD OF THE INVENTION

This invention relates to an apparatus for enzyme detection, and, more particularly, relates to a flow-through enzyme detection system for high speed liquid chromatography.

BACKGROUND OF THE INVENTION

It is oftentimes necessary to separate and detect enzymes. This is particularly true, for example, in medical applications where isoenzyme profiles are useful for diagnostic purposes.

Enzymes have heretofore been separated and many techniques have heretofore been suggested and/or utilized to achieve such separation. Examples of separation techniques may be found, for example, in U.S. Pat. Nos. 3,722,181, 3,808,125 and 3,983,299.

Likewise, separated enzymes have been heretofore detected, and detection of such enzymes has normally included incubating the enzyme with an appropriate substrate and then monitoring the formation of the product after a fixed reaction time.

One of the more useful high speed techniques for separating enzymes utilizes liquid chromatographic column technology. More recent advances in this type of separation have made it possible to resolve enzyme mixtures in about ten minutes or less. For example, the five isoenzymes of lactic acid dehydrogenase have been resolved in six minutes and the three isoenzymes of creatine phosphokinase have been resolved in four minutes.

High speed separation of isoenzymes is of particular significance because of the clinical utility of isoenzyme profiles in diagnosing miocardial infarction, pulmonary infarctions, and liver diseases. If coupled into a flow-through system with a dependably fast and accurate enzyme detection system, then high speed liquid chromatography of isoenzymes can become a clinically useful analytical tool.

Heretofore, however, two major problems have been encountered in the design and construction of chromatographic flow-through enzyme detectors. One of these problems is distortion by band spreading of the chromatographic profile in the detector and the other is demixing of enzymes and substrate during passage through the system.

Detectors heretofore known and/or utilized have attempted to overcome these problems but have not been completely successful, at least in many respects. One such attempt, for example, has been made to overcome these problems by utilization of instruments that segment the liquid reactant stream with air bubbles. This alternating gas-liquid segmentation prevents intersegmental mixing while still allowing intersegmental mixing of reactants, but obviously does not permit continuous flow-through of a mixture of separated enzymes and substrate.

Thus, while enzyme detectors have heretofore been suggested, none has been completely successful in providing high performance systems that provide dependably fast and accurate detection.

SUMMARY OF THE INVENTION

This invention provides an apparatus for enzyme detection that is well suited for high performance liquid chromatography utilizing a flow-through system.

It is therefore an object of this invention to provide an apparatus for enzyme detection.

It is another object of this invention to provide a flow-through system for detection of enzymes.

It is still another object of this invention to provide an enzyme detector for high performance liquid chromatography.

It is still another object of this invention to provide a flow-through enzyme detector that is dependably fast and accurate.

It is yet another object of this invention to provide a flow-through enzyme detector that minimizes chromatographic profile distortion due to band spreading in the detector.

It is yet another object of this invention to provide a flow-through enzyme detector that prevents enzyme substrate demixing during passage through the detector.

It is still another object of this invention to provide a flow-through enzyme detector that includes a reaction bed for receiving separated enzymes and a reaction causing substrate, as well as a detector for detecting the reacted enzymes coupled from the reaction bed.

It is still another object of this invention to provide an improved system for automatically detecting enzymes utilizing a flow-through enzyme detector.

It is still another object of this invention to provide an improved system for automatically separating and detecting enzymes.

It is yet another object of this invention to provide an improved system for automatically detecting enzymes that includes a separation column to separate enzymes, a mixer for mixing separated enzymes and a substrate, a reaction chamber to react enzymes with the substrate, a monitor to detect the reacted enzymes, and read-out means to indicate the detected enzymes.

With these and other objects in view, which will become apparent to one skilled in the art as the description proceeds, this invention resides in the novel construction, combination and arrangement of parts substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a combined block and perspective view of the apparatus of this invention for detecting enzymes shown incorporated in an improved system for automatically separating and detecting enzymes;

FIG. 2 is a perspective view of the reaction chamber of the enzyme detector of this invention as shown in FIG. 1 with portions broken away to illustrate the packing material therein;

FIGS. 3A and B illustrate tracings of commercial trypsin samples showing non-use and use, respectively, of the enzyme detector of this invention;

FIGS. 4A and B illustrate chromatograms of nucleotide mixtures showing non-use and use, respectively, of the enzyme detector of this invention;

FIG. 5 is a graph illustrating the linearity of the system of this invention;

FIG. 6 is a graph showing the particular linearity of the system of this invention at a low enzyme concentration;

FIGS. 7A and B illustrate UV and activity tracings, respectively, of enzyme detector results for commercial calf alkaline phosphatase utilizing the system of this invention;

FIGS. 8A and B illustrate activity tracings of enzyme detector activity of three CPK isoenzymes utilizing the system of this invention; and FIGS. 9A and B illustrate activity tracings of detected enzyme activity of LDH isoenzymes utilizing the system of this invention.

DESCRIPTION OF THE INVENTION

As brought out hereinabove, detection of enzymes has heretofore been accomplished by incubating an enzyme with an appropriate substrate and monitoring the formation of product after a fixed reaction time. When the appropriate substrate concentration (S) is much greater than the constant ($K_m$) in the Michaelis-Menten equation, which is $$K_m = (S)(\frac{V\max}{v} - 1),$$

then the maximum reaction velocity Vmax is proportional to the enzyme concentration (v). Since the reaction rate is independent of substrate, the reaction is zero-order with respect to the substrate. This results in a linear accumulation of product with time. As the substrate is depleted, however, the reaction becomes first-order with respect to the substrate and may not be used to determine enzyme concentration. The apparatus of this invention is a fixed time flow-through enzyme detector that maintains zero-order reaction kinetics with respect to substrates during enzyme detection.

In addition, the apparatus of this invention overcomes the two major problems in the design and construction of chromatographic flow-through enzyme detectors and, in particular, provides a detector that minimizes chromatographic profile distortion by band spreading within the detector and the prevention of enzyme substrate demixing during passage through the system. The apparatus of this invention overcomes the foregoing problems through use of a packed column reaction bed as a part of the detector apparatus.

Band spreading in packed separation columns is well understood. Parameters such as particle size, mobile phase velocity, solute diffusion coefficients, and stationary phase properties have all been found to influence solute band spreading in a separation system. It must be noted, however, that the packed chromatography column used for separation purposes and the packed flow-through enzyme detector are functionally different. The chromatography column is intended to separate compounds while the flow-through detector must prevent any separation of the components of a mixture. To achieve this end (i.e. prevention of component separation), it is necessary to eliminate all those features in the flow-through detector (or reactor) support that could cause any separation of the components in the mixture passing therethrough. This includes use of a packing material that is completely inert to all compounds so that no solute partition occurs. Along with the elimination of partitioning, it is also necessary to eliminate the possibility of reactant demixing through differential rates of diffusion. To promote uniform rates of diffusion, all stagnant mobile phase pools are sought to be eliminated and this is largely achieved through the use of a non-porous, organic packing material, and spherical beads have been found to be preferred for use as packing material. If no packing material is used, streaking on the chamber walls can occur, and the liquid in the center of the column moves faster than liquid in wall contact. This must be avoided or at least minimized in order to achieve the desired end.

An overall system 12 for separation and detection of enzymes is shown in FIG. 1. As shown, system 12 includes a pair of columns 14 and 15 with column 14 being a separation column designed for chromatographic separation of enzymes while column 15 is a reaction chamber employed as an enzyme reaction bed. Columns 14 and 15 are connected by conduits 17 and 18 connected to one another through union tee 19 the third connection to which is connected the substrate pump 21 through conduit 22 and through which substrate is supplied to the system. The mixing of substrate and separated enzymes (both in liquid form) occurs at the union tee 19 under pressure and no special mixing device need be used.

As also shown in FIG. 1, enzyme samples to be tested are injected into conduit 24 at injection junction 25, which junction is connected with pumps 26 through conduit 27. Pumps 26 supply buffer material under pressure and thus cause the enzymes to be forced under pressure through the separation column 14, and through conduits 17 and 18 to reaction bed 15. Substrates are supplied under pressure to the separated enzymes at tee 19 prior to introduction into the reaction bed 15.

After the introduction of substrate to the separated enzymes at tee 19, reaction takes place in reaction bed 15 during the flow of the mixture through the reaction chamber 15. It has been found preferable that the pressure applied is just sufficient to maintain a constant flow rate through the chamber with the reaction taking place for a predetermined period of time during flow through the chamber. The reacted end product is coupled from the reaction chamber 15 through conduit 28 to detector 30, after which the product is discarded through exhaust conduit 31. Detector 30 is preferably a spectrophotometer and the end product (which assumes color during reaction as is well known) is thus preferably measured spectrophotometrically after it is eluted out from the reaction chamber 15. As shown, spectrophotometer 30 is connected with a recorder 33 through lead 34 to make a permanent record of detected enzymes.

Pumps 21 and 26, spectrophotometer 30, and recorder 33 may all be conventional. Pumps 26 may be, for example, a Model 384 Isco Dial-o-grad pumping system, while pump 21 may be, for example, a high pressure Isco syringe pump. Spectrophotometer 30 may be, for example, a Perkin Elmer LC 55 or Aminco Fluoromonitor. Conduits 17, 18, 24, 27, 28 and 31 are preferably flexible steel tubings of sufficient diameter to handle the flow rate desired and may be, for example, 1/16 inch outside diameter (O.D.) and 0.02 inch inside diameter (I.D.), while chambers 14 and 15 are also preferably stainless steel tubes, as in tee 19 (which may be, for example, a 1/16 inch standard tee).

The substrate to be added is selected from known substrates useful to cause a reaction for paticular enzymes to be detected. In like manner, the buffer is selected from known conventional buffers. The buffer, or carrier, maintains the pH at a constant value, as is known. Examples of substrates and buffers that have been utilized with specific enzymes are set forth by way of example hereinafter. As also can be readily appreciated, where it is necessary to obtain a spectrophotometrically measured end product by use of a series of coupling enzyme reactions, all of the substrates necessary to cause such reaction must be included into the mixture at tee 19. Detection of enzymes could also be achieved by monitoring absorption or fluorescence, for example, and the detector could be a conventional detector measuring such characteristics as refractive index, optical rotation, or the like.

The separation column 14 may be any conventional column suitable for separating enzymes in a known manner. Column 14 may thus be a column such as described in U.S. Pat. Nos. 3,722,181 and 3,808,125. Preferably, however the separation column is a column such as described in copending U.S. patent application Ser. No. 537,197 entitled "Bonded Carbohydrate Stationary Phases for Chromatography."

The isoenzymes to be detected may be prepared into a sample in any conventional fashion and it is only important that they be separated by the separation columns so that when substrate is mixed therewith a reaction can occur in the reaction chamber.

The function of the reaction chamber is to provide a matrix for enzyme reactions to occur. An ideal reaction chamber facilitates maximum enzyme reaction yet keeps band spreading to a minimum. Enzyme reactions can be optimized by controlling the reaction temperature, by controlling the reaction time, and by preselection of the proper substrates. Band broadening can be caused by poor efficiency of the reaction chamber, separation of enzymes from their substrates, or products created or added by the chamber or bed itself. This latter effect is particularly important since it often results in unidentifiable peaks.

In the reaction detector of this invention, the reaction bed includes packing material 38 that is packed within chamber 15 (to normally fill the same) to form the reaction bed within the chamber as shown in FIG. 2. The reaction chamber and packing material preferably includes small particle packing material with good packing procedures being utilized, and has minimum volume in all outside column tubings and connectors. In addition, the packing materials utilized generate minimum chromatographical separation between all substances passing through the column. This includes size separation, absorption, ion exchanging processes, etc. Selection of a proper packing material (which material may have a chemical coating thereon) is necessary in order to achieve a reaction bed suitable for the enzyme detector of this invention.

In selecting a packing material, several materials were tested. Table I shows the reaction time of various compounds by reaction beds packed with different packing materials. The flow rate and column dimensions were constant in all cases. Table I is as follows:

TABLE I

| Samples | 40Å CPG | 100Å Lichrosorb CPG | Borosilicate Glass | | | Sodasilica | |
|---|---|---|---|---|---|---|---|
| | | | NP Corning | GTS NP Corning | EPON NP Corning | NP Ra | GTS NP Ra |
| TAME | 302.3 | 427.0 | >600 | — | — | 137.2 | 132.5 |
| PDA | 291.0 | 351.0 | >600 | 398.8 | 283.0 | 133.9 | 130.1 |
| PNP | 152.3 | 189.6 | 171.4 | 168.8 | 169.8 | 134.3 | 130.2 |
| TS | 134.8 | 178.5 | 151.2 | 145.6 | 139.5 | 135.7 | 131.0 |
| NPP | 129.6 | 158.9 | 137.7 | 138.6 | 135.7 | 133.9 | 130.8 |
| Myo | 133.5 | >600 | 141.3 | 136.9 | 134.1 | 138.1 | 129.7 |
| Try | 129.2 | 148.2 | 136.9 | 138.0 | 135.3 | — | — |
| Album | 127.1 | 118.4 | 133.9 | 135.8 | 132.8 | 132.5 | 129.1 |
| AL | 128.0 | 119.3 | 135.4 | 136.9 | 133.5 | 132.5 | 126.6 |

TAME - tosylarginine methyl ester
PDA - p-phenylenediamine
PNP - p-nitrophenol
TS - p-toluenesulfonic acid
NPP - nitrophenylphosphate
Myo - myoglobin
Try - trypsin
Album - albumin
AL - alkaline phosphatase The reaction bed must be packed with a non-porous inorganic material that does not interact with substrates, enzymes, or products. Glass beads have been found to be preferred, but small non-porous inorganic particles other than beads can be utilized. For glass beads or other particles utilized, a range of about 5 to 400 millimicron nominal diameter can be utilized with a range of about 5 to 200 millimicron nominal diameter being more preferred and a range of 37 to 74 millimicron nominal diameter being most preferred as presently known. With 5 micron beads the pressure drop through the chamber would be on the order of several thousand pounds, however, while the pressure drop for 400 micron beads would be in the order of only about 50 pounds or less. For the preferred 37-74 millimicron beads, the pressure drop is about 120 pounds in a 60 cm column.

Porous supports are not desirable because they tend to separate enzymes (large molecules) from their substrates and products (small molecules) by molecular sieving. These effects are demonstrated in Table I by the fact that when run on a reaction bed packed with 100 Å CPG glass, small compounds have much longer retention times than large ones. The best packing material, on the other hand, will have substantially the same reaction time for all samples. It should be noted that, as shown in Table I, the 40 Å CPG glass (controlled porosity glass) has less size discrimative effect than the 100 Å Lichrosorb silica. This is due to the very small pore volume of the 40 Å glass (less than 0.1 ml per gram).

As also shown in Table I, borosilicate glass materials are not preferred for the reaction bed because they have large amounts of negative groups ($BO_3^-$, $SIO^-$) on the surface and tend to retain positive charged compounds much longer than neutral or ionic compounds. 40 Å CPG and 100 Å Lichrosorb materials also have this effect although to some less extent. Table I also shows that covering the packing materials with GTS (glycidoxytrimethoxypropylsilane) or EPON (triglycidylglycerol) coatings decreases, but does not eliminate, all of the ion exchange interaction. GTS coatings are sold by Dow Corning under the name "Z6040," while EPON coatings are sold by Shell Chemical as "EPON 812."

Sodasilicate non-porous glass, on the other hand, shows very little change in the size discriminative properties and hence may be used very successfully as packing material for enzyme reaction beds. GTS coated non-porous sodasilicate glass is also shown in Table I to be a very satisfactory packing material.

GTS and EPON coated glass may be prepared as follows:

GTS coated glass may be prepared in the same manner as described in my U.S. Pat. No. 3,983,299 entitled "Bonded Carbohydrate Stationary Phases for Chromatography" wherein controlled porosity glass was treated. For coating of non-porous glass, the particles (which are preferably beads) are treated at 100° C. for 4 hours with a solute containing 90 ml of toluene and 10 ml of glycidoxypropl trimethoxysilane. The suspension is then filtered and washed with 100 ml volumes of ethanol and water. The epoxide is converted to the diol by a 30 minute treatment at pH 2. After a final wash with water and ethanol the glycerol-bonded support is dried in vaccuo.

EPON coated glass may be prepared in the same manner as described in U.S. Pat. No. 4,029,583 of Frederick E. Regnier and Shung-Ho Chang entitled "Chromatographic Supports and Methods and Apparatus for Preparing the Same". For coating of non-porous glass, GTS glass (prepared as above set forth) is added to a glass chromatographic column (such as a 2"×38" column for example) fitted with a 10 micron glass frit above a narrowed portion. A nitrogen gas cylinder is connected through a passage to a T joint at the bottom of the column and the column support bed fluidized with a reverse flow of nitrogen. 50 ml of diethyl ether containing 500 mg of Epon 812 (triglycidyl glycenol) is added to the support and nitrogen is continued until all of the ether evaporates and the diglycidylethylene glycol controlled support is then again tumbled in a fluidized bed. The nitrogen flow is temporarily interrupted and a flask (such as a 50 ml double necked round bottom flask) containing 25 ml of $BF_3$ etherate is fitted onto the bottom of the column. The nitrogen stream is connected to the second joint of the flask so that the support bed is again fluidized in addition to supplying $BF_3$ etherate vapor into the fluidized bed. Polymerization of the oxirane monomer is completed in about 15 minutes at 25° C.

The rate of enzyme-catalyzed reactions generally increases with temperature within the temperature range in which the enzyme is stable and retains full activity, as is generally true for most chemical reactions. Thus, the detector of this invention can be utilized at any temperature above the freezing point and below the denaturization temperature of the enzyme to be detected.

The enzyme reaction is dependent upon the time of the reaction so that a longer reaction time allows more products to form and hence provides greater sensitivity for the system. Longer reaction times can be achieved by increasing the length or diameter of the reaction bed. Unfortumately, this also is accomplished not only by the sacrifice of time economy but also by band broadening.

A proper choice of column dimensions is necessary. Tables II and III list the retention time, enzyme activity and band width of alkaline phosphatase detected by passing through reaction beds with different lengths and diameters, as follows:

TABLE II

| Column Length (cm) | I.D. (mm) | Retention Time (sec) | Peak Width (sec) | Relative Enzyme Activity x |
|---|---|---|---|---|
| 20 | 4.8 | 67.9 | 21.26 | 1 |
| 40 | 4.8 | 117.0 | 25.43 | 1.78 |
| 60 | 4.8 | 167.2 | 28.82 | 2.56 |

Flow Rate: Column - 1.37 ml/min
Substrate - .70 ml/min 2mM Mg $Cl_2$
Buffer: 50 mH borate buffer pH = 8
Sample: 0.2 mg/ml Alkaline Phosphatase (Hog) 275 µl
Substrate: 4mH p-NP p-nitrophenylphosphate
Reaction Bed: GTS 37-74µ non-porous sodasilicate glass
Temp: Room Temperature

TABLE III

| I.D. mm | Column Length mm | Column Volume cm³ | Retention Time sec | Peak Width sec | Relative Enzyme Activity x |
|---|---|---|---|---|---|
| 4 | 25 | 3.142 | 54.4 | 23.62 | 1 |
| 5 | 25 | 4.909 | 09.9 | 28.82 | 1.60 |
| 7 | 25 | 9.621 | 144.9 | 30.71 | 2.41 |
| 8 | 25 | 12.566 | 176.8 | 33.07 | 3.50 |

Enzyme: 0.2 mg/ml Alkaline Phosphate (hog intestine)
Flow Rate: 2.075 ml/min from column
1.37 ml/min from substrate pump
Buffer: 0.05M borate (pH = 8) .2 mM Mg $Cl_2$
Substrate: 4mM p-nitrophenyl phosphate in above buffer
Flow Rate: 1.3 ml/min from column
0.7 ml/min from substrate
Reaction Bed: 34-74µ GTS non-porous Sodasilicate glass
Temp: Room Temperature Enzyme activity is approximately proportional to the reaction time yet the band width increases only a small fraction when a larger reaction column is utilized. It is felt that since the eluent spends time in the tubing and connectors outside the reaction column, this accounts for the fact that the reaction time, as shown in Table II, did not double when increasing the reaction column length from 20 to 40 centimeters.

It is felt that the reaction chamber can be from about 1 cm to several meters in length with the internal diameter of the column being about 2 to 8 millimeters with 3 or 4 millimeters being optimum.

One way to evaluate the band broadening effect caused by the reaction column is to compare chromatograms run with and without the reaction column included in the system. FIG. 3A shows the UV tracing of a commercial trypsin sample separated by a 37µ-74µ particle DEAE glycophase/CPG column while FIG. 3B shows the UV tracing performed under the same conditions except passing through an extra 60×0.48 cm reaction column packed with 37-74µ particle sodasilica glass. A similar comparison was made between the chromatograms of the nucleotide mixture separated by 10μ particle DEAE glycophase/CPG column with a reaction column (FIG. 4A) and without a reaction column (FIG. 4B). It might be noted that the band broadening effect as shown in FIG. 3 is more significant than the effect as shown FIG. 4.

It is important in a detecting system that the detector response has a linear relationship over a known range to the amount of sample injected. FIG. 5 demonstrates the linearity of the system of this invention. FIG. 5 shows, within the useful O.D. range, that the relation is essentially linear. The peak height is used to express enzyme activity since all peaks have identical peak width. The following was utilized in developing the relationships as shown in FIG. 5:

| | |
|---|---|
| Flow Rate: | Column - 1.37 ml/min |
| | Substrate - .70 ml/min |
| Buffer: | 5mH borate buffer pH = 8, 2mH Mg Cl$_2$ 1M NaCl (isocratic) |
| Sample: | Alkaline phosphatase (Hog intestinal mucosa) 275 μl |
| Substrate: | 4mM p-nitrophenylphosphate in buffer |
| Column: | 60 × .5 cm DEAE 200/400 250 Å CPG |
| Reaction Bed: | 40 × .5 cm 5% EPON coated non-porous sodasilicate glass |
| Column Pressure: | Approximately 50 Psi |
| Detector: | 410 nm |

This linear relationship is shown in FIG. 6 to exist even at a very low enzyme concentration. To increase the sensitivity, testing with Alkaline phosphates (hog intestinal) was done at elevated temperatures with larger reaction columns as follows:

| | |
|---|---|
| Flow Rate: | Column - 1.37 ml/min |
| | Substrate - .70 ml/min |
| Buffer: | (a) Tris 0.05 M pH = 8 |
| | (b) Tris 0.05 M pH = 8 .03M Nacl |
| Substrate: | 4mM p-nitrophenylphosphate in buffer |
| Sample: | Alkaline phosphatase (hog intestine) |
| Column: | Nil |
| Reaction Bed: | .8 × 27 cm GTS 37μ non-porous sodasilicate glass |
| Temp: | 60° C. water bath |
| Column Pressure: | ~30 Psi |
| Detector: | 410 nm |

In operation, the sample to be detected for enzymes is injected (at sample injection point 25, as by a conventional syringe, for example) into the buffer solution being pumped by pumps 26 to and through the system. The enzymes are then separated at separation column 14 after which the separated enzymes (carried by the buffer) are mixed (at tee 19) with a proper substrate to cause reaction to occur. The mixture is then pumped through a reaction chamber 15 where the reaction occurs during passage of the mixture through chamber 15. The reaction of the substrate with the separated enzymes will cause the product to have a specific color (or other characteristics) which is then detected by a monitoring means 30 (such as a spectrophotometer). This indication of detected enzymes is then recorded. Thus, a constant flow is established through the separation column, reaction chamber, and spectrophotometer during which solute separation, reaction and detection automatically occurs without interruption of flow.

This invention was successfully utilized to separate commercially available calf intestinal alkaline phosphatase. FIG. 7A is a UV tracing of the commercial calf alkaline phosphatase and indicates the many components. FIG. 7B is the activity tracing of the enzyme and this tracing shows that only a small fraction of the enzyme preparation has the alkaline phosphatase activity. The amount of sample injected for the UV tracing of FIG. 7A was twenty times more and the recorder at a sensitivity ten times higher than that used for the activity tracing of FIG. 7B. It can therefore be appreciated that monitoring enzyme activity is far more superior than is monitoring its UV absorption. The parameters utilized for enzyme detection as shown by FIG. 7 were as follows:

| Alkaline Phosphatase (Hog) | |
|---|---|
| Flow Rate: | Column - 1.37 ml/min |
| | Substrate - .35 ml/min |
| Buffer: | (a) Tris 9.05 M pH = 8 |
| | (b) (a) +0.3 M Nacl |
| Substrate: | 8 mM P-nitrophenylphosphate |
| Sample Rate: | 270 μl |
| Column: | .5 × 50 cm 37-74μ DEAE/CPG |
| Reaction Bed: | .5 × 60 cm GTS 37-74μ non-porous sodasilicate glass |
| Column Pressure: | 250 Psi |
| Detector: | (A) 280 nm 5mV |
| | (B) 410 nm 50 mV |

Separation of CPK enzymes is shown in FIG. 8 which shows the activity tracings of three CPK isoenzymes. The identity of each peak was verified by a standard electrophoresis technique. It demonstrates that the separation and assay of isoenzyme activity can be done as fast as fifteen minutes without human tedium and error in collecting an assay of each fraction. The parameters utilized for detection of CPK enzymes are as follows:

| | |
|---|---|
| Flow Rate: | Column - (A) 2.74 ml/min (B) 1.37 ml |
| | Substrate - 1.4 ml/min 0.7 ml |
| Buffer: | (a) 0.05M Tris, 0.05 Na cl, ME 10$^{-3}$M, Ph = 7 |
| | (b) 0.05M Tris, 0.3 M Na cl, ME 10$^{-5}$M, Ph = 7 |
| Substrate: | 20 mM creatine —P, 1.5 mM ADP, 3 mM glucose, 0.8 mM NADP, 2.7 mM AMP 2.5 mM glutathione, Hexokinase, G-6-P deHase in 0.1M Tris pH = 6.8 Mg SO$_4$ .03M buffer solution |
| Sample: | 275μl CPK isoenzymes |
| Column: | .5 × 60 cm DEAE 200/400 250 Å CPG |
| Post Column: | .5 × 40 cm 5% EPON coating on 37-74μ non-porous sodasilicate glass |
| Column Pressure: | (A) ~450 Psi (B) ~Psi |
| Detector: | 340 nm, 10 mV |

Finally LDH isoenzymes have been separated as shown by FIGS. 9A and 9B. This shows that the separation assay can be done in as short as twenty minutes and that the identity of each peak was also verified by a standard electrophoresis technique except for the extra peak appearing between LD 3 and LD 2. The parameters utilized for detection of LDH isoenzymes were as follows:

| | |
|---|---|
| Flow rate: | Column - (A) 2.74 ml/min (B) 1.37 ml/min |
| | Substrate - 1.4 ml/min .7 ml/min |
| Buffer: | a) .02 M Tris 6 pH = 8.01 |
| | b) .025 M Tris pH = 8.0 0.2M Nacl |
| Substrate: | .279 M lactate; 0.001M-NAD .1% albumin |
| | in Tris 0.05 M pH = 8.8 |
| Sample: | 275 µl LDH isoenzymes |
| Column: | .5 × 60 cm DEAE 200/400 250 Å CPG |
| Post Column: | .5 × 40 cm 5% EPON coating on 37µ–74µ |
| | non-porous sodasilicate glass |
| Column Pressure: | (A) ~450 Psi (B) ~250 Psi |
| Detector: | 340 nm, 10 mV (20mV) |

In view of the foregoing, it will be appreciated that this invention provides a novel apparatus for detecting enzymes that is particularly well suited for use as a flow-through enzyme detector system for high speed liquid chromatography.

What is claimed is:

1. A detection apparatus, comprising:
   mixing means for receiving and mixing, in liquid form, a compound having at least one enzyme to be detected and reacting material for said enzyme;
   fluid inlet means for receiving, in liquid form, said mixed compound and reacting material from said mixing means;
   reaction enabling means including a chamber substantially filled with particles the surface of each of which is nonporous and inorganic with said reaction enabling means being connected with said fluid inlet means for receiving said compound and reacting material therefrom in liquid form with the mixture thereof being caused to pass through said chamber of said reaction enabling means in a continuous flow whereby said mixture is brought into containing contact with the surface of said particles while in said chamber and whereby reaction of said enzyme with said reacting material continues for a predetermined period of time, said reaction enabling means providing a reaction product output after said predetermined period of time with said reaction product output having a characteristic indicative of detected enzyme; and
   monitoring means connected with said reaction enabling means to receive said output therefrom, said monitoring means responsive to said characteristic in said output providing an indication of said detected enzyme.

2. The apparatus of claim 1 wherein said particles having non-porous and inorganic surfaces are beads of a size between about 5 and 400 millimicrons nominal diameter.

3. The apparatus of claim 2 wherein said beads are nonporous inorganic sodasilicate glass beads.

4. The apparatus of claim 1 wherein said particles having nonporous and inorganic surfaces are beads of a size between 37 and 74 millimicrons nominal diameter.

5. The apparatus of claim 1 wherein said apparatus forms a part of a high performance liquid chromatography system.

6. A detection apparatus, comprising:
   separation means for receiving a compound and separating a plurality of enzymes therein to be detected;
   fluid inlet means for receiving, in liquid form, from said separation means, said compound having said separated plurality of enzymes therein to be detected and reacting material for said enzymes;
   reaction enabling means including a chamber substantially filled with particles the surface of each of which is nonporous and inorganic with said reaction enabling means being connected with said fluid inlet means for receiving said compound and reacting material therefrom in liquid form with the mixture thereof being caused to pass through said chamber of said reaction enabling means in a continuous flow whereby said mixture is brought into continuing contact with the surface of said particles while in said chamber and whereby reaction of said enzymes with said reacting material continues for a predetermined period of time, said reaction enabling means providing a reaction product output after said predetermined period of time with said reaction product output have a characteristic indicative of detective enzymes; and
   monitoring means connected with said reaction enabling means to receive said output therefrom, said monitoring means responsive to said characteristic in said output providing an indication of said detected enzymes.

7. A detection apparatus, comprising:
   fluid inlet means for receiving, in liquid form, a compound having at least one enzyme to be detected and reacting material for said enzyme;
   reaction enabling means including a chamber substantially filled with particles the surface of each of which is nonporous and inorganic beads of a size between about 5 and 400 millimicrons nominal diameter having a glycidoxypropl trimethoxysilane coating thereon, with said reaction enabling means being connected with said fluid inlet means for receiving said compound and reacting material therefrom in liquid form with the mixture thereof being caused to pass through said chamber of said reaction enabling means in a continuous flow whereby said mixture is brought into continuing contact with the surface of said particles while in said chamber and whereby reaction of said enzymes with said reacting material continues for a predetermined period of time, said reaction enabling means providing a reaction product output after said predetermined period of time with said reaction product output having a characteristic indicative of detected enzymes; and
   monitoring means connected with said reaction enabling means to receive said output therefrom, said monitoring means responsive to said characteristic in said output providing an indication of said detected enzymes.

8. An apparatus for detecting enzymes in a mixture during continuous flow of said mixture through said apparatus, said apparatus comprising:
   separating means for separating enzymes in a liquid solution and supplying the same under pressure from said separating means;
   substrate supplying means for supplying a substrate capable of reacting with said separated enzymes, said substrate being in liquid form and supplied under pressure from the output of said substrate supplying means;
   mixing means including a tee one input of which is connected to the output of said separating means to receive said liquid solution under pressure therefrom and the other input of which is connected to the output of said substrate supplying means to receive said substrate under pressure therefrom whereby mixing occurs at said tee so that said mixing means provides an output in liquid form that is a mixture of said received liquid solution and substrate;

a reaction chamber substantially filled with particles the surface of each of which is nonporous and inorganic, said chamber being connected with said mixing means and receiving said output in liquid form therefrom for passage through said chamber and into contact with the surface of said particles, said substrate reacting with said enzymes during passage through said reaction chamber so that the reaction product output from said chamber has a characteristic indicative of detected enzymes; and monitoring means connected with said reaction chamber to receive the reaction product output therefrom, said monitoring means respective to said characteristic in said output providing an indication of said detected enzymes.

9. The apparatus of claim 8 wherein said particles within said reaction chamber are glass beads of between about 5 and 400 millimicrons nominal diameter and whereby the pressure drop through said chamber is between about fifty and several thousand pounds.

10. For an enzyme detection apparatus, a reaction device comprising a chamber substantially filled with particles the surface of each of which is nonporous and inorganic glass beads having a glycidoxypropl trimethoxysilane coating thereon and having a range of between about 37 and 74 millimicrons nominal diameter whereby separated enzymes may be reacted with substrate during passage through said chamber and into contact with the surface of said particles without appreciable band spreading of the chromatographic profile or demixing of enzymes and substrate during passage through an enzyme detection apparatus.

11. The device of claim 10 wherein said particles are glass beads having a range of between about 5 and 400 millimicrons nominal diameter.

12. A flow-through system for detecting enzymes in a liquid solution, said system comprising:

separation means for separating enzymes in a received liquid solution and providing an output in liquid form with said enzymes separated therein;

substrate supply means for supplying substrate capable of reacting with said separated enzymes;

mixing means separately connected with said separation means and said substrate supply means to receive the outputs in liquid form therefrom and providing an output in liquid form that is a mixture thereof;

a reaction chamber substantially filled with particles the surface of which is non-porous and inorganic, said chamber being connected with said mixing means and receiving said output therefrom in liquid form for passage through said chamber and into contact with the surface of said particles, said substrate reacting with said enzymes during passage through said reaction chamber so that the reaction product output from said chamber has a color characteristic indicative of detected enzymes;

a spectrophotometer connected with said reaction chamber to receive the reaction product output therefrom, said spectrophotometer responsive to said color characteristic in said reaction product output providing an indication of said detected enzymes; and pump means connected with said separation means and said substrate supply means whereby a continuous flow is established through said system during detection of said enzymes.

13. The system of claim 12 wherein said pump means pumps buffer solution to said separation means, wherein said system includes means for permitting injection of a sample containing enzymes into said buffer prior to receipt of said liquid solution at said separation means, and wherein said system includes a pen recorder connected with said spectrophotometer to record enzymes injected into said solution and detected during passage through said system.

* * * * *